(12) United States Patent
Gleich

(10) Patent No.: US 11,045,107 B2
(45) Date of Patent: Jun. 29, 2021

(54) DEVICE AND METHOD FOR EXAMINATION AND USE OF AN ELECTRICAL FIELD IN AN OBJECT UNDER EXAMINATION CONTAINING MAGNETIC PARTICLES

(71) Applicant: KONINKLIJKE PHILIPS N.V., Eindhoven (NL)

(72) Inventor: Bernhard Gleich, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 2085 days.

(21) Appl. No.: 13/972,983

(22) Filed: Aug. 22, 2013

(65) Prior Publication Data
US 2013/0338481 A1 Dec. 19, 2013

Related U.S. Application Data

(62) Division of application No. 10/552,808, filed as application No. PCT/IB2004/050448 on Apr. 15, 2004, now Pat. No. 8,532,735.

(30) Foreign Application Priority Data

Apr. 15, 2003 (EP) .................................... 03101023

(51) Int. Cl.
*A61B 5/00* (2006.01)
*A61B 5/0536* (2021.01)
(Continued)

(52) U.S. Cl.
CPC .......... *A61B 5/0536* (2013.01); *A61B 5/0036* (2018.08); *A61B 5/05* (2013.01);
(Continued)

(58) Field of Classification Search
CPC .......... A61N 1/372; A61N 1/406; A61B 5/05; A61B 5/0515; A61B 5/0536; A61B 5/4836
See application file for complete search history.

(56) References Cited

U.S. PATENT DOCUMENTS 4,155,352 A 5/1979 Toglia
4,617,939 A 10/1986 Brown
(Continued)

FOREIGN PATENT DOCUMENTS

DE 19514515 A1 11/1996
DE 19516323 A1 11/1996
(Continued)

OTHER PUBLICATIONS

Bervas, Katarina, Electric Current Density Imaging of Bone by MRI, Magnetic Resonance Imaging, vol. 15, No. 8, pp. 909-915 (1997). (Year: 1997).*

(Continued)

*Primary Examiner* — Rajeev P Siripurapu

(57) ABSTRACT

Aspects of the present invention relate to a device and method for examining and using an electrical field in a magnetic gradient field, containing magnetic particles in an examination area of an object under examination, including introducing magnetic particles into at least part of the examination area of the object under examination; generating an electrical field at least in part of the examination area; generating a magnetic field having a spatial magnetic field strength profile with a first sub-zone with a low magnetic field strength and a second sub-zone with a higher magnetic field strength in the examination area; varying a spatial position of the two sub-zones in the examination area such that a magnetization of the particles changes locally; detecting signals which depend on the magnetization in the examination area influenced by this variation; evaluating the (Continued)

Figure 1:
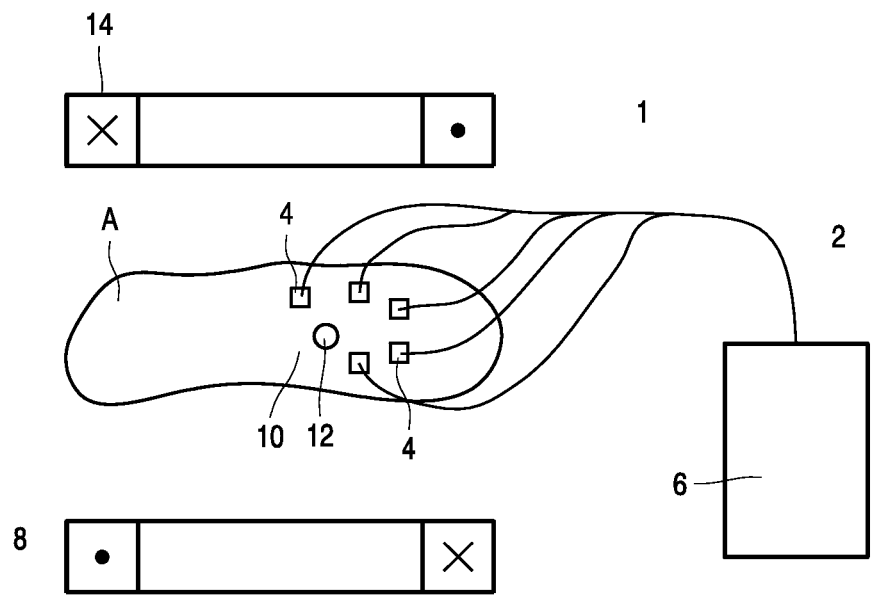

signals to obtain information about the spatial distribution of the magnetic particles in the examination area; and determining a conductivity in the examination area as a function of a magnetization status of the magnetic particles.

20 Claims, 1 Drawing Sheet

(51) Int. Cl.
    *A61B 5/05*          (2021.01)
    *A61N 2/02*          (2006.01)
    *A61K 49/00*        (2006.01)
    *A61B 5/0515*       (2021.01)
    *A61N 1/372*        (2006.01)
    *A61N 1/40*          (2006.01)

(52) U.S. Cl.
    CPC .......... *A61B 5/0515* (2013.01); *A61B 5/4836* (2013.01); *A61K 49/00* (2013.01); *A61N 1/372* (2013.01); *A61N 2/02* (2013.01); *A61N 1/406* (2013.01)

(56) References Cited

U.S. PATENT DOCUMENTS

| | | | |
|---|---|---|---|
| 4,731,239 A * | 3/1988 | Gordon | G01R 33/5601 424/9.32 |
| 4,810,401 A | 3/1989 | Mair | |
| 5,224,922 A * | 7/1993 | Kurtz | A61N 2/02 128/898 |
| 5,587,657 A * | 12/1996 | Kanazawa | G01R 33/56554 324/307 |
| 5,612,019 A * | 3/1997 | Gordon | A61K 9/5094 424/646 |
| 5,639,444 A | 6/1997 | Klaveness | |
| 5,672,879 A * | 9/1997 | Glavish | H01J 37/1475 250/396 ML |
| 5,733,525 A | 3/1998 | Klaveness | |
| 5,746,999 A | 5/1998 | Gries | |
| 5,794,622 A | 8/1998 | Chopp | |
| 5,928,958 A | 7/1999 | Pilgrimm | |
| 6,082,366 A * | 7/2000 | Andra | A61B 5/06 128/899 |
| 6,120,856 A * | 9/2000 | Liberti | A61K 9/5094 252/62.56 |
| 6,168,780 B1 | 1/2001 | Andrae | |
| 6,236,886 B1 | 5/2001 | Cherepenin | |
| 6,346,196 B1 * | 2/2002 | Bose | B03C 1/01 209/214 |
| 6,470,220 B1 | 10/2002 | Kraus | |
| 6,583,624 B1 * | 6/2003 | Muthupillai | G01R 33/56308 324/306 |
| 6,638,494 B1 | 10/2003 | Pilgrimm | |
| 6,726,650 B2 | 4/2004 | Schneider | |
| 6,940,286 B2 | 9/2005 | Wang | |
| 7,439,736 B2 | 10/2008 | Meaney | |
| 7,553,283 B2 | 6/2009 | Sandrin | |
| 7,619,408 B2 * | 11/2009 | Gleich | A61B 5/0515 324/204 |
| 2002/0138019 A1 | 9/2002 | Wexler | |
| 2002/0159951 A1 | 10/2002 | Unger | |
| 2003/0085703 A1 | 5/2003 | Gleich | |
| 2004/0092839 A1 | 5/2004 | Shin | |
| 2004/0258762 A1 * | 12/2004 | Boppart | A61K 9/1694 424/491 |
| 2013/0192349 A1 * | 8/2013 | Ramkumar | G01N 29/022 73/54.41 |

FOREIGN PATENT DOCUMENTS

| | | |
|---|---|---|
| DE | 69308324 T2 | 6/1997 |
| DE | 69316993 T2 | 5/1998 |
| FR | 2660864 A1 | 10/1991 |
| WO | 199409699 A1 | 5/1994 |
| WO | 199956788 A1 | 11/1999 |
| WO | 200006244 A2 | 2/2000 |
| WO | WO 03043931 A1 * | 5/2003 .............. F16K 13/10 |

OTHER PUBLICATIONS

Levy, Shai et al "Electromagnetic Impedance Tomography (EMIT): A New Method for Impedance Imaging", IEEE Transaction on Medical Imaging, vol. 21, No. 6, Jun. 2002.

Sprandel, U. et al "Magnetically Responsive Erythrocyte Ghosts", Methods in Enzymology, vol. 149, 1987.

Danilov, Yu. N. et al "Concentration of Erythrocyte-based Magnetic Carriers in the Bloodstream", Bulletin of Experimental Biology and Medicine: A Publ. Fo the Academy of Medical Sciences of the USSR. 1986.

\* cited by examiner

DEVICE AND METHOD FOR EXAMINATION AND USE OF AN ELECTRICAL FIELD IN AN OBJECT UNDER EXAMINATION CONTAINING MAGNETIC PARTICLES

This application is a divisional of U.S. patent application Ser. No. 10/552,808, filed on Oct. 11, 2005, which is a National Stage Application of PCT/IB2004/050448, filed on Apr. 15, 2004, and which claims the benefit of European Patent Application No. 03101023.4, filed on Apr. 15, 2003. The entire contents of each of these application are incorporated herein by reference.

The present invention relates to a device for examination and use of an electrical field in a magnetic gradient field containing magnetic particles in an examination area of an object under examination. The invention also relates to a method of determining the conductivity or the, especially three-dimensional, conductivity distribution in an examination area of an object under examination using a device according to the invention, a method for drug release, especially in locally targeted manner, in an examination area of an object under examination using a device according to the invention, as well as use of the device according to the invention to determine the conductivity or the, especially three-dimensional, conductivity distribution in an examination area, and for targeted release of active ingredients and for electro-stimulation. The invention further relates to an electro-physiologic contrast composition, to a method for the manufacture of said contrast composition and to a method for imaging electric resistivity or conductivity in an examination area in particular to a method for imaging internal electric fields using the electro-physiologic contrast composition according to the invention.

To be able to make the most accurate statements possible about the conductivity of in particular areas of tissue of living organisms, it is currently common to use impedance tomography. This method as a rule only supplies information about an area close to the surface, and not about the electrical behavior of deeper layers of tissue or organs. In addition, the reliability and resolution of this measuring method leave something to be desired, especially if it is desired to display differences in conductivity in spatially resolved manner.

For example, DE 693 16 993 T2 follows the approach of reducing the effects stemming from the geometry of a body under examination by applying electrical scanning signals to the body at different frequencies. It has emerged from this that the change over time in the impedance associated with different dynamic features of the body is a function of frequency. To be able to make a reliable statement about frequency dependency, it is then necessary to differentiate again, with which dynamic feature the change in impedance is associated.

The images obtainable with electrical impedance tomography are generally obtained by means of a back-projection method described in U.S. Pat. No. 4,617,939. This method has the disadvantage that the reliability of image reproduction reduces towards the middle of the image due to a decreasing signal-to-noise ratio. To improve image reproduction or resolution, DE 693 08 324 T2 proposes to apply electrical input signals successively through at least one pair of electrodes attached to the body, wherein the measurements are effected at varying time intervals. This procedure inevitably only attempts to reduce the shortcomings of an existing method, without bringing about any substantial improvement.

It was therefore an object of the present invention to provide a device and a method which do not suffer from the disadvantages of the prior art and which allow reliable and accurate high-resolution conductivity measurements even at a distance from the surface.

Accordingly, a device for examination and use of an electrical field in a magnetic gradient field, containing magnetic particles in an examination area of an object under examination, was discovered which comprises a) at least one first arrangement for determining the spatial distribution of magnetic particles in at least one examination area of the object under examination, comprising a means for generating a magnetic field with such a spatial magnetic field strength profile that a first sub-zone with low magnetic field strength and a second sub-zone with higher magnetic field strength are produced in at least one examination area, a means for detecting signals which depend on the magnetization in the object under examination, especially in the examination area, influenced by a local change in the particles, together with a means for evaluating the signals to obtain information about the, especially time-variable, spatial distribution of the magnetic particles in the examination area; and b) at least one second arrangement, comprising at least one electrical transmit and/or receive unit, comprising at least one voltage generator, at least one terminal contact connected to the voltage generator and applicable and/or fastenable to an object under examination, and a ground terminal especially connected to the voltage generator and applicable and/or fastenable to an object under examination.

The second arrangement may comprise at least one pair of contact electrodes, especially a plurality of pairs of contact electrodes, for recording potential differences. In one embodiment, the second arrangement thus comprises a measuring device known from impedance tomography.

In another development, the device according to the invention also preferably comprises at least one voltage measuring unit and/or current measuring unit.

In addition, it has proven expedient for the voltage generator, the voltage measuring unit and/or the current measuring unit to be capable of being brought into active connection or to be at least temporarily connected with a microprocessor or computer.

Particularly defect-free image reproduction is achieved as a rule when the voltage measuring unit and/or the current measuring unit is/are equipped with at least one analog filter, measuring amplifier, A/D converter and/or a digital filter.

The voltage generator is appropriately equipped in such a way that, via electrodes connected thereto, an electrical input signal may be applied to at least one electrode pair, which allows a potential difference between further pairs to be picked off at terminal contacts. According to a preferred embodiment, a measuring voltage in the range of from 10 to 200 V may be generated with the voltage generator.

Furthermore, according to the invention a device may be used of the type which comprises at least one frequency converter.

In addition, according to a further aspect of the invention, devices may also be used of the type which comprise a means, in particular at least one coil arrangement, for changing the spatial position of the two sub-zones in the examination area, such that the magnetization of the particles varies locally.

A particularly suitable device according to the invention is also distinguished by a coil arrangement for receiving signals induced by the variation over time of the magnetization in the examination area.

The object forming the basis of the invention is additionally achieved by a method of determining the, especially spatially resolved, conductivity, especially the three-dimensional conductivity distribution, in an examination area of an object under examination using a device according to the invention, comprising the introduction of magnetic particles into at least part of an examination area of the object under examination, generation of an electrical field at least in part of the examination area, generation of a magnetic field with such a spatial magnetic field strength profile that a first sub-zone with low magnetic field strength and a second sub-zone with higher magnetic field strength are produced in the examination area, variation of the spatial position of the two sub-zones in the examination area, such that the magnetization of the particles changes locally, the detection of signals which depend on the magnetization in the examination area influenced by this change, evaluation of the signals to obtain information about the, especially time-variable, spatial distribution of the magnetic particles in the examination area, and determination of the conductivity in the examination area as a function of the magnetization status and/or the orientation of the magnetic particles.

Satisfactory results in the examination of living organisms, especially the human body, are obtained in particular when the magnetic measuring voltage lies in the nanoVolt range, especially above 5 nV, more preferred above 30 nV.

According to a further aspect of the invention, a method is proposed for, especially locally targeted, drug or active ingredient release in an examination area of an object under examination using a device according to the invention, comprising the introduction of magnetic particles into at least part of an examination area of the object under examination, generation of an alternating electrical field at least in part of the examination area, generation of a magnetic field with such a spatial magnetic field strength profile that a first sub-zone with low magnetic field strength and a second sub-zone with higher magnetic field strength are produced in the examination area, variation of the spatial position of the two sub-zones in the examination area, such that the magnetization of the particles changes locally, in particular by means of superimposition of an oscillating or rotating magnetic field, wherein magnetic particles are used whose magnetic reversal is effected predominantly by means of geometric (Brownian) rotation or oscillation and which at least partially comprise an outer shell of an electrophoresis gel, which contains at least one drug or active ingredient with at least one charged functional group, wherein the oscillation or rotational frequency of the magnetic field is matched to the frequency of the electrical field in such a way that the charge of the functional group of the active ingredient experiences a constant electrical field.

According to a particularly preferred development, the frequency of the alternating electrical field lies in the range of from approximately 100 Hz to approximately 500 kHz, in particular in the range of from approximately 10 kHz to approximately 200 kHz, and the oscillation or rotational frequency of the magnetic particles lies in the range of from approximately 100 Hz to approximately 1 MHz, preferably from approximately 1 kHz to approximately 1 MHz and in particular from approximately 10 kHz to approximately 500 kHz. According to an expedient development of the invention, the ratio of the frequency of the alternating electrical field to the rotational or oscillation frequency of the magnetic particle is expressed substantially as an integer.

Magnetic particles are appropriately used, of which at least some exhibit anisotropic properties, especially effective anisotropy.

One development may be characterized in that the effective anisotropy of the magnetic particles exhibits a value which is sufficient for the magnetic reversal of the particles to take place substantially by geometric (Brownian) rotation.

It is particularly preferable for magnetic particles to be used which constitute monodomain particles, whose magnetic reversal is effected substantially by means of Brownian rotation or oscillation.

In a further embodiment, the magnetic particles used constitute hard- or soft-magnetic multidomain particles.

The magnetic particles preferably comprise hard-magnetic materials.

Examples of suitable hard-magnetic materials are Al—Ni, Al—Ni—Co and Fe—Co—V alloys and barium ferrite (BaO 6x$Fe_2O_3$).

Particularly good measurement results are obtained when the magnetic particles, in particular the ferromagnetic particles, are in the form of lamellae with low conductivity or needles with high conductivity.

It has been demonstrated that, with the devices according to the invention, conductivity and the, especially three-dimensional, conductivity distribution may be determined in the examination area of an object under examination with high resolution and reliability.

The device according to the invention is additionally suitable to be used for targeted electrostimulation, especially of neural pathways or muscles. In order to stimulate neural pathways in targeted manner, it is common these days, especially in the treatment of pain, to use so-called Transcutaneous Electrical Nerve Stimulation (TENS) (c.f. "Die Schmerzhilfe" ("Analgesia"), the journal of Deutsche Schmerzhilfe e.V., Hamburg, 1999). With this method, a current with a frequency in the range of from 1 to 10 Hz or from 60 to 100 Hz is applied as appropriate via adhesive electrodes. A disadvantage of this method is the small penetration depth. In addition, an optimum application site has to be sought for the adhesive electrodes used for each individual case of treatment, if the desired effect is to be achieved at all.

Accordingly, a method was discovered of, especially locally targeted, electrostimulation in an examination area of an object under examination using a device according to the invention, comprising the introduction of magnetic particles into at least part of an examination area of the object under examination, generation of an alternating electrical field at least in part of the examination area, generation of a magnetic field with such a spatial magnetic field strength profile that a first sub-zone with low magnetic field strength and a second sub-zone with higher magnetic field strength are produced in the examination area, variation of the spatial position of the two sub-zones in the examination area, such that the magnetization of the particles changes locally, especially by means of superimposition of an oscillating or rotating magnetic field, wherein magnetic particles are used whose magnetic reversal is effected predominantly by means of geometric rotation or oscillation and wherein the electrical field in the examination area is converted from a higher-frequency field into a lower-frequency field by interaction with the rotating or oscillating particles.

It is now also possible, with the device according to the invention or with the method according to the invention, to stimulate deeper-lying areas of the body without having to exercise particular caution as to how and where an electrode has precisely to be applied. In so doing, use is made of the fact that an electrical field, which is of a high frequency for the purposes of electrostimulation and which also penetrates into deeper body layers, may be specifically downconverted in localized manner by controlled rotation or oscillation of the magnetic particles present in the examination or stimulation area into a lower-frequency electrical field, which is suitable for stimulating neural pathways or portions of the musculature. For example, an electrical field with a frequency ranging from approximately 100 Hz to approximately 100 kHz, for example with frequencies of at least 3 kHz, may be downconverted by rotation or oscillation of the magnetic particles to frequency ranges of approximately 1 to 500 Hz, in particular from 1 to 100 Hz. It goes without saying that frequency ranges, such as for example from 1 to 10 Hz or from 60 to 100 Hz, may also be selected. As a rule, the conductivity or the resistance in the examination area permeated by the magnetic particles is specifically manipulated by means of the orientation of the these particles relative to the electrical field. It is advantageous, in this respect, that the sub-zone with low magnetic field strength may be of only small spatial extent in the gradient field and, in addition, may be readily displaceable in the examination area. In this way, electrostimulation may be performed in a body in a very effectively localized manner.

The first arrangement of the device according to the invention substantially makes use of an arrangement as described in unpublished German patent application bearing file no. 101 51 778.5. Reference is thereby made to the above-mentioned patent application also for preferred embodiments of this arrangement.

With the arrangement used according to the invention, a spatially non-homogeneous magnetic field is generated in the examination area. In the first sub-zone, the magnetic field is so weak that magnetization of the particles deviates to a greater or lesser extent from the external magnetic field, i.e. is not saturated. This first sub-zone is preferably a spatially cohesive zone; it may be a punctiform zone, but may also be a line or an area. In the second sub-zone (i.e. in the rest of the examination area outside the first sub-zone), the magnetic field is sufficiently strong to keep the particles in a state of saturation. Magnetization is saturated if magnetization of virtually all the particles is oriented in roughly the direction of the external magnetic field, such that, as the magnetic field is increased further, magnetization increases substantially less there than in the first sub-zone in the event of a corresponding increase in the magnetic field.

By changing the position of the two sub-zones within the examination area, the (overall) magnetization in the examination area is varied. Therefore, if the magnetization in the examination area or physical parameters influenced thereby are measured, information may be derived therefrom about the spatial distribution of the magnetic particles in the examination area.

To change the spatial position of the two sub-zones in the examination area or to change the magnetic field strength in the first sub-zone, it is possible, for example, to generate a locally and/or time-variable magnetic field. Provision may also be made for the signals induced in at least one coil by the variation over time of the magnetization in the examination area to be received and evaluated to obtain information about the spatial distribution of the magnetic particles in the examination area. The largest possible signals may be achieved in that the spatial position of the two sub-zones is varied as rapidly as possible. To detect the signals, a coil may be used with which a magnetic field is generated in the examination area. However, it is preferable to use at least one separate coil.

If the change in the spatial position of the sub-zones proceeds for example by means of a time-variable magnetic field, a similarly periodic signal is induced in a coil. Reception of this signal may prove difficult, however, if the signals generated in the examination area and the time-variable magnetic field are active at the same time; therefore, it is not readily possible to distinguish between the signals induced by the magnetic field and the signals induced by changing the magnetization in the examination area. However, this may be avoided in that a time-variable magnetic field in a first frequency band acts on the examination area and, from the signal received in the coil, a second frequency band, which preferably comprises higher frequency components than the first frequency band, is evaluated to obtain information about the spatial distribution of the magnetic particles. In this regard, use is made of the fact that the frequency components of the second frequency band may only arise through variation of the magnetization in the examination area as a consequence of the non-linearity of the magnetization characteristic. If the time-variable magnetic field has a sinusoidal periodic profile, the first frequency band consists of only a single frequency component—the sinusoidal fundamental oscillation. On the other hand, the second frequency band also comprises higher harmonics (so-called harmonic waves) of the sinusoidal fundamental oscillation as well as said fundamental oscillation, which harmonics may be used for evaluation.

A preferred arrangement for the method according to the invention is distinguished in that the means for generating the magnetic field comprise a gradient coil arrangement for generating a magnetic gradient field which reverses direction in the first sub-zone of the examination area and exhibits a zero crossing. If the gradient coil arrangement comprises, for example, two similar windings arranged both sides of the examination area but flowed through by currents in opposite directions (Maxwell coil), this magnetic field is zero at a point on the winding axis and increases in virtually linear manner either side of this point with opposing polarity. Only in the case of the particles located in the area around this field zero point is the magnetization not saturated. The particles outside this area are magnetized to saturation.

An arrangement may be provided with means for generating a time-variable magnetic field superimposed on the magnetic gradient field for the purpose of displacing the two sub-zones in the examination area. The area generated by the gradient coil arrangement is displaced around the field zero point, i.e. the first sub-zone, within the examination area by the time-variable magnetic field. If this magnetic field has a suitable time profile and orientation, the field zero point may in this way pass through the entire examination area.

The change in magnetization accompanying displacement of the field zero point may be received with an appropriate coil arrangement. The coil used to receive the signals generated in the examination area may be a coil which already serves to generate the magnetic field in the examination area. It is also advantageous, however, to use a separate coil for reception, because the latter may be decoupled from the coil arrangement which generates a time-variable magnetic field. In addition, though an improved signal-to-noise ratio may be achieved with one coil, this is even more the case with a plurality of coils.

The amplitude of the signals induced in the coil arrangement is the greater, the more quickly the position of the field zero point changes in the examination area, i.e. the more quickly the time-variable magnetic field superimposed on the magnetic gradient field changes. However, it is technically difficult, on the one hand to generate a time-variable magnetic field whose amplitude is sufficient to displace the field zero point at the point of the examination area and whose rate of change is sufficiently great to generate signals with a sufficient amplitude. Arrangements which are particularly well suited to this purpose are those with means for generating a first and at least one second magnetic field superimposed on the magnetic gradient field, wherein the first magnetic field may be varied slowly over time with a high amplitude and the second magnetic field may be varied rapidly over time with a low amplitude. Two magnetic fields are then generated, preferably by two coil arrangements, which may vary at different rates and with different amplitudes. As a further advantage, the field changes may be so rapid (e.g. >20 kHz) that they lie above the limit of audibility for humans. The two magnetic fields in the examination area may also extend substantially perpendicularly to one another. This allows displacement of the field-free point in a two-dimensional area. This may be expanded to a three-dimensional area by a further magnetic field with a component which extends perpendicularly to both magnetic fields. An arrangement is likewise advantageous which has a filter connected in series with the coil arrangement, which filter suppresses those signal components of the signal induced in the coil arrangement which are in a first frequency band and accepts those signal components which are in a second frequency band comprising higher frequency components than the first frequency components. In this regard, use is made of the fact that the magnetization characteristic is not linear in the area in which the magnetization passes from the unsaturated into the saturated state. This non-linearity has the effect that, for example, a temporally sinusoidally extending magnetic field with the frequency f in the area of non-linearity causes time-variable induction with the frequency f (fundamental wave) and integer multiples of the frequency f (harmonic waves or higher harmonics). Evaluation of the harmonic waves has the advantage that the fundamental wave of the magnetic field effective at the same time for displacement of the field-free point does not have any influence on evaluation.

According to the invention, the magnetic particles become saturated when an external magnetic field is applied, in particular one with a strength of approximately 100 mT or less. It goes without saying that larger saturation field strengths are also suitable for the method according to the invention.

Indeed, suitable magnetic field strengths for many applications are approximately 10 mT or less. This strength is sufficient for many tissue and organ examinations. However, good measurement results are achieved even with field strengths in the range of 1 mT or less or of approximately 0.1 mT or less. For example, in the case of magnetic field strengths of approximately 10 mT or less, of approximately 1 mT or less and of approximately 0.1 mT or less, very precise conductivity values may be obtained with high spatial resolution.

An external magnetic field, in which the magnetic particles pass into or are present in the saturated state, should be understood for the purposes of the present invention to mean a magnetic field in which approximately half the saturation magnetization has been achieved.

Suitable magnetic particles are those which may enter saturation in a sufficiently small magnetic field. A necessary prerequisite therefore is that the magnetic particles have a minimum size or a minimum dipole moment. For the purposes of the present invention, the term magnetic particles consequently also covers magnetizable particles.

Suitable magnetic particles appropriately have dimensions which are small relative to the size of the voxels whose magnetization it is desired to determine using the method according to the invention. Moreover, the particles should preferably be magnetized to saturation with the smallest possible field strengths of the magnetic field. The smaller is the field strength required therefor, the higher is the spatial resolution capacity or the weaker may be the (external) magnetic field to be generated in the examination area. Furthermore, the magnetic particles should have the highest possible dipole moment or high saturation induction, so that the change in magnetization results in the largest possible output signals. When the method is used for medical examinations, it is also important for the particles not to be toxic.

According to a preferred development of the method according to the invention, it is proposed that the magnetic particle be a monodomain particle, which may undergo magnetic reversal substantially by means of Brownian rotation and in which Néel rotation contributes at most in a subordinate manner to magnetic reversal.

Suitable magnetic monodomain particles are preferably so dimensioned that only a single magnetic domain (the monodomain) may form therein or Weiss domains are absent. According to a particularly preferred variant of the invention, suitable particle sizes lie in the range of 20 nm to approximately 800 nm, wherein the upper limit also depends on the material used. Magnetite ($Fe_3O_4$), maghemite ($\gamma$-$Fe_2O_3$) and/or non-stoichiometric magnetic iron oxides are preferably used for monodomain particles.

In general, it is advantageous for the monodomain particles to exhibit moderate effective anisotropy. Effective anisotropy is here understood to mean the anisotropy resulting from shape anisotropy and from average crystalline anisotropy. In the above case, the change in direction of magnetization is always accompanied by rotation of the particles, unlike in the case of magnetic reversal by means of Néel rotation. Monodomain particles with a high effective anisotropy are preferably used, so ensuring that magnetic reversal is effected by Brownian or geometric rotation or oscillation when an external magnetic field is applied.

In an alternative embodiment of the method according to the invention, the magnetic particle may be a hard- or soft-magnetic multidomain particle. These multidomain particles are generally relatively large magnetic particles, in which a number of magnetic domains may form. Such multidomain particles suitably have low saturation induction.

Hard-magnetic multidomain particles exhibit substantially the same magnetic properties as monodomain particles with high effective anisotropy. Soft-magnetic multidomain particles with low saturation magnetization have the advantage that they may be of any desired shape in order to be able to be used in the method according to the invention. They are preferably needle- or rod-shaped.

The invention also relates to an electro-physiologic contrast composition for magnetic particle imaging comprising electro-physiologic contrast particles that are capable of inducing anisotropic electric conductivity in the examination area and that comprise one or more magnetic particles. The electrophysiologic contrast particles can either be composed of a non-conductive material creating anisotropic conductivity or by a conductive material inducing anisotropy by guiding in an anisotropic way the electric field lines. The electro-physiologic contrast composition can be used in the method according to the invention to improve the contrast in the imaging using an electrical field or even to image internal magnetic fields even with out and applied external electrical fields, for example the internal electric fields of a heart. The composition can be used in various forms, for example in powder form or in emulsion form.

In particular, it is preferred that in the electro-physiologic contrast composition the electro-physiologic contrast particles have a main magnetic anisotropic direction and a main electric anisotropic direction which main magnetic anisotropic direction and main electric anisotropic direction are correlated such that, when the electric contrast particles align their main magnetic direction in an external magnetic field, also their electric anisotropy direction is at least partly aligned. With correlation is meant that when the electro-physiologic contrast particles are aligned in a magnetic field by aligning the magnetic particles, also an electric anisotropy is induced. The main magnetic anisotropic direction can be perpendicular, but is preferably parallel with the main electric anisotropic direction.

Electric anisotropic properties can be achieved in various different ways. In a preferred embodiment the electro-physiologic contrast particle has an anisotropic shape, preferably a disc like shape, of a material having a low conductivity that is covered with magnetic particles or a coating of a magnetic material. In case of a coated particle the coating must have a magnetic anisotropy and must not destroy the electric insulating properties of the disk. In this embodiment the anisotropic shape of the low conductive disc imparts the anisotropic electric conductivity. The disc may be any flat shape but preferably is circular flat shape.

Preferably, the ratio of the diameter to the thickness of the disc is between 0.005 and 0.8, preferably between 0.01 and 0.5. The higher the ratio, the higher the contrast effect per unit mass of the electro-physiologic contrast composition. The advantage is that a smaller amount of the composition is required to achieve a good imaging contrast. For application a living organism, the diameter of the disc is preferably below 10 micrometers to not block the blood flow in the small blood vessels.

On application of a magnetic field in the examination area, the magnetic particles on the low conductive disc force the contrast particles to align and cause anisotropic conductive properties in the examination area, which influences the applied external electrical fields. The local differences in conductive properties can be used to create an image. This can be done by using an external electric field or, in a special embodiment of the invention, even without an external electric field, using the electrical fields in the body, for example on a heart. In order to achieve imaging of internal electric fields the concentration of the magnetic contrast particles in the contrast composition and also in the examination area must be high. In particular for this application it is preferred that the disc having a low conductivity is a red blood cell. In this way a large amount of electro-physiologic contrast composition can be introduced in the body without detrimental effect.

In another embodiment of the electro-physiologic contrast composition according to the invention the electric contrast particles are needle shaped conductive multi-domain magnetic particles. In this embodiment the anisotropic conductivity is created because the conductive anisotropic shaped particles guide the electric field lines preferentially along the long axis of the particle. The advantage of this embodiment is that a lower amount of the contrast composition is needed is to create sufficient electric contrast effect. This embodiment is useful in technical applications. In medical applications it is preferred that the needle shaped electric contrast particle is covered with a thin and conductive coating to prevent damage to blood vessels or tissue. A coating of organic material is preferred. For medical applications it is further preferred, that the needle shaped magnetic particles are composed of a number of small magnetic iron oxide or iron metal particles assembled to a needle shaped particle which particles touch each other to have the required conductivity, but relatively easily break down in the examination area to increase the speed of metabolisation.

In view of the requirements that the contrast particles can rotate in an applied to external magnetic field it is preferred that, the magnetic particles are predominantly anisotropic magnetic particles having an average internal anisotropy field of at least 2 mT, preferably at least 3, most preferably at least 5 mT. However, in view of obtaining a good contrast in the imaging of the magnetic particles, it is preferred that the magnetic particles in the contrast particles also comprise isotropic soft magnetic particles. Preferably, the magnetic particles are semi-hard or hard magnetic particles having a high anisotropy, can only reverse in an applied external magnetic field by geometric rotation, but reach a high magnetization saturation required to provide sufficient torque to rotate the contrast particle.

The invention also relates to a method for imaging internal electric fields in a living organism, wherein at least 10 weight %, preferably 20 weight %, of the red blood cells in the blood of a patient are modified to form an electro-physiologic contrast composition. The invention further relates to a process for the manufacture of an electro-physiologic contrast composition according to the invention, comprising aligning particles having electric anisotropic properties along a main electric anisotropic direction and depositing magnetic particles on said electric anisotropic particles in the presence of a magnetic field. Preferably, in the above method the particles having electric anisotropic properties are disc shaped particles of a non conductive material, which disc shaped particles are aligned along a main electric anisotropic direction by depositing them substantially flat on a surface and wherein subsequently magnetic particles are deposited on the disc shaped particles in the presence of a magnetic field.

The invention further relates to a method for imaging electrical resistivity or conductivity in an examination area comprising the steps of applying electrodes for generating and measuring electrical fields, introducing an electro-physiologic contrast composition according to the invention into the examination area, create an electrical field, scanning the examination area with the field free region according to the method according to the invention and recording signals from the electric measurement electrodes as a function of the position of the field free point to spatially resolve the electrical conductivity or resistivity in the examination area.

Further, in another embodiment the invention relates to a method for imaging internal electrical fields in an examination area comprising the steps of applying electrodes for measuring electrical fields, introducing an electro-physiologic composition according to the invention, scanning the examination area with the field free region according to the method according to the invention and recording signals from the electric measurement electrodes as a function of the position of the field free point to spatially resolve the internal electrical fields in the examination area.

In general the magnetic particles in the magnetic particle administering composition, are chosen such that good magnetic particle images, in particular a good resolution can be obtained in a given field gradient. In unpublished German patent application number 101 51778.5 a magnetic particle imaging method is described. It is generally described that magnetic mono-domain particles having a size between 20 and 800 nanometres or a glass beat coated with a magnetic coating can be used in this method. However, in order to achieve a good magnetic imaging contrast and resolution at relatively low magnetic field gradients, improved magnetic particle compositions are highly desirable. The inventors have found magnetic particles having improved magnetic particle imaging properties.

Preferably, the magnetic particles in the magnetic particle administering composition have a magnetization curve having a step change, the step change being characterized in that the magnetization change, as measured in an aqueous suspension, in a first field strength window of magnitude delta around the inflection point of said step change is at least a factor 3 higher than the magnetization change in the field strength windows of magnitude delta below and/or in the field strength windows of magnitude delta above the first field strength window, wherein delta is less than 2000 microtesla, preferably less than 1000 microtesla, and wherein the time in which the magnetisation step change is completed in the first delta window is less than 0.01 seconds, preferably less than 0.005 sec, more preferably less than 0.001, most preferably less than 0.0005 seconds. It has been found, that such magnetic particles are particularly suitable for magnetic particle imaging, in particular for obtaining a good resolution of the image. It is further preferred, that the magnetic particle composition has a magnetisation curve, wherein the step change is at least 10%, preferably at least 20%, more preferably at least 30% and most preferably at least 50% of the total magnetisation of the particle composition as measured at an external magnetisation field of 1 Tesla. It is further preferred, that the magnetization change in the first field strength window of magnitude delta around the inflection point of said step change is at least a factor 4, preferably at least a factor 5 higher than the magnetization change in the field strength windows of magnitude delta below or in the field strength windows of magnitude delta above the first field strength window.

The magnetic particle composition is particularly useful for use in a magnetic particle imaging technique. The particles show good spatial resolution at relatively low field strength gradients. Further, the magnetic particle composition allows for a relatively high scanning speed for examining a large examination area. For example, for application in medical magnetic particle imaging, where the step change occurs preferably at a delta value below 1000 microTesla, the particle composition has a resolution value better than between 0.1 and 10 mm at magnetic field strength gradients between 10 and 0.1 T/m. With the magnetic particle imaging technique using the magnetic particle compositions according to the invention extremely good resolution can be obtained, for example in a range from 0.1 to 10 micrometres in applications, where are very high magnetic field is gradients can be achieved, for example in microscopy. It is noted that strictly speaking, magnetic field strength is expressed in H (A/m). However, in the present application, when reference is made to magnetic field strength, B-fields are meant. A magnetic fields B of 2000 µT as described above corresponds to an H field of 2 mT/$\mu_0$=1.6 kA/m, that is the equivalent H field that would produce a B field of 2 mT in vacuum.

Preferably, the magnetic particles in the electro-physiologic contrast compositions according to the invention and the method according to the invention as described above comprise magnetic particles that meet the specified step change requirements of the magnetic particle composition according to the invention as described above.

A method for measuring the magnetisation curve and the required step change is as follows. A sample of a magnetic particle composition is suspended in water, optionally with the help of a simple detergent. To prevent clumping and/or to de-agglomerate the magnetic particles an ultrasound treatment possible can be used. The concentration of the magnetic particle composition is less than 0.01 gr core mass per liter of solvent. With core mass is meant the mass of the magnetic material in the magnetic particle composition. The suspension is brought into a fast magnetometer. (i.e. a device that measures the magnetization of the sample while an external field is applied). Suitable fast magnetometers are known to the expert. The magnetometer is equipped with means allowing to produce an external field at the sample position in at least two orthogonal directions simultaneously, i.e. to produce any magnetic field below a given maximum amplitude and a given maximum speed of change. The magnetisation is measured also in at least two orthogonal directions in the same plane.

First the saturation magnetisation is measured. For this, a magnetic field of about one Tesla is applied in one direction and the magnitude of magnetization is measured after at least 10 seconds. Then the measurement sequences for determining the step change starts. The sequence starts with choosing a field vector with an external field magnitude below 20 mT. This field is applied for at most 100 seconds. Then a second direction is chosen. This direction defines the scalar values of the field H and the magnetization M. The field is rapidly changed, preferably less than 1 millisecond, so that it lies now in −H direction with some magnitude below 20 mT. Then the field is changed from −H to +H e.g. in a linear way and the (now scalar i.e. projected) magnetization is recorded. The magnetization curve is recorded in less than 0.01 s but longer than 1 µs. Where the magnetisation curve shows a step change, a first window of size delta is positioned centrally on the inflection point of the magnetisation step change. Similarly, a window of size delta is positioned below and above the first window, and the required step change is evaluated by determining the change in magnetisation in each of the windows.

Whether or not a given magnetic particle composition has the required step change depends in a complicated way on many variables, for example of the size of the particles, the particle size distribution, the shape of the particles, the damping constant for Neel rotation, the type of magnetic material, the crystallinity and the stochiometry of the composition of the magnetic material. It has been found that it is particularly important that the particle size distribution of the particle composition is narrow. Preferably, the magnetic particle composition according to the invention has a narrow particle size distribution wherein at least 50 weight % of the particles have a particle size between plus or minus 50%, preferably 25%, more preferably 10% of the average particle size. Preferably, the amount of particles within the specified windows, is at least 70 wt %, preferably at least 80 wt %, and most preferably at least 90 wt %. Particularly good results are obtained with mono-domain particles have a low magnetic anisotropy with a field needed for inducing Neel rotation of substantially below 10 mT, preferably below 5 mT, more preferably below 2 mT. Preferably, the magnetic particles are mono-domain particles having an average particle size between 20 and 80 nanometres, more preferably between 25 and 70 nanometres, must preferably between 30 and 60 nanometres, wherein at least 50, preferably at least 60, more preferably at least 70 weight % of the particles have a particle size between the average particle size plus or minus 10 nanometre.

In an alternative embodiment of the magnetic particle composition according to the invention, the magnetic particle is a multi-domain particle having substantially a needle shape having a demagnetisation factor of less than 0.001.

This magnetic particle composition is particularly useful in non-medical applications where the needles shape is not a disadvantage. In another alternative embodiment, the magnetic particle composition according to the invention comprises magnetic particles comprising a non-magnetic core covered with a magnetic coating material, wherein the thickness of the coating is between 5 and 80 nanometres and wherein the demagnetisation factor is less than 0.01 and a diameter below 300 µm. Also in these alternative embodiments it is advantageous to have a small particle size distribution as described above. The physical parameters of the magnetic particles in these embodiments are preferably chosen to meet the step change requirement as described above for achieving good imaging properties.

The magnetic particle composition according to the invention can be manufactured by first forming magnetic particles, for example by precipitation, for example by contacting a solution comprising ferrous and ferric ions with a solution comprising sodium hydroxide as described above. In principle, a known precipitation process can be used. It is also possible to grind the particles from bulk material, for example using a high speed ball mill. The essential next step for obtaining a good magnetic particle composition is the selection and separation of the particles. The first step is to perform a size selection process by filtering and/or centrifuge methods. The next step is to perform a selection process based on the magnetic properties of the particles, for example, using oscillating magnetic gradient fields.

The present invention is based on the surprising discovery that conductivity may be determined with high resolution in objects under examination, especially in bodies of living organisms. In this respect, it is of particular advantage that the conductivity values may be assigned to very precisely and closely defined areas in the object under examination. It is thus possible, with simple apparatus, to obtain good conductivity images even of deeper-lying tissue with high imaging accuracy and to be able to represent changes in the state of the tissue very precisely.

It is additionally advantageous that active ingredients or drugs may be released in a targeted manner. To this end, it is sufficient to use a device such as is also used to determine the spatially resolved conductivity measurement. All that is needed for this is to use active ingredients, which comprise a charged functional group in the molecule and are contained in a coating, especially a layer of electrophoresis gel, surrounding the magnetic particle, and to match the rotation behavior of the magnetic particles to the frequency of the alternating electrical field. In this way, active ingredients may be released in targeted manner at a locally closely defined treatment site. For example, active ingredients may be used which may be damaging to healthy tissue as the initial embedding of the active ingredients in the gel layer surrounding the magnetic particle allows risk-free transport to the site of use without the active ingredient being released prematurely. This makes targeted treatment of tumors or metastases possible, for example.

The invention will be further described with reference to examples of embodiment shown in the drawings to which, however, the invention is not restricted. In the Figures FIG. 1 is a schematic representation of a device according to the invention with an object under examination; and FIG. 2 is a schematic representation of a transmitting and measuring unit according to the invention.

FIG. 1 shows a device 1 according to the invention, comprising an arrangement 2, provided for determining the conductivity in an object under examination A, and an arrangement 8 for generating a localized, field-free or weak-field point or zone 12. The arrangement 2 for determining the conductivity in an object under examination A has a plurality of surface contact electrodes 4 on the surface of the object under examination, which are arranged in such a way that a desired examination area is detected. Each contact 4 is connected with a schematically represented transmit and receive unit 6. The transmit and receive unit 6 is explained in detail below with reference to FIG. 2. The object under examination A is located in the arrangement 8, with which a magnetic gradient field comprising a sub-zone with higher field strength 10 and a locally variable sub-zone 12 with lower field strength is generated at least in the object under examination A by means of a Maxwell coil arrangement 14. Magnetic or magnetizable particles introduced into the object under examination may be brought to saturation or magnetically reversed in the sub-zone 12 by superimposition of an additional magnetic field or by local variation of the sub-zone 12, a situation which may be readily detected by means of the coil arrangement 14 or other, separate coil arrangements (not shown). Given that, by using magnetic particles which may be magnetically reversed primarily by geometric rotation or oscillation, the conductivity behavior in an object under examination may be manipulated at least slightly, a conductivity signal received via the transmit and receive unit 6 may be precisely located when the precise position of the sub-zone 12 in the object under examination is known. The transmit and receive apparatus 6 used may be equipped with suitable filters, which, for example, suppress the transmitting frequencies or frequency bands of the arrangement 8 or of the voltage generators 22 of the transmit and receive unit 6 (c.f. FIG. 2). Analog filters, digital filters, measuring amplifiers and/or A/D converters may be used here for example, on their own or in any desired combination. With the device illustrated in FIG. 1, comprising the arrangements 2 and 8, it is possible to obtain both a spatially highly resolved image of the conductivity distribution in object A and perform locally controlled electrophoresis or electrostimulation. For this purpose, the transmitter power of the unit 6 should optionally be increased in relation to the conductivity measurement and the receive part of the unit 6 may be dispensed with.

Figure 2:
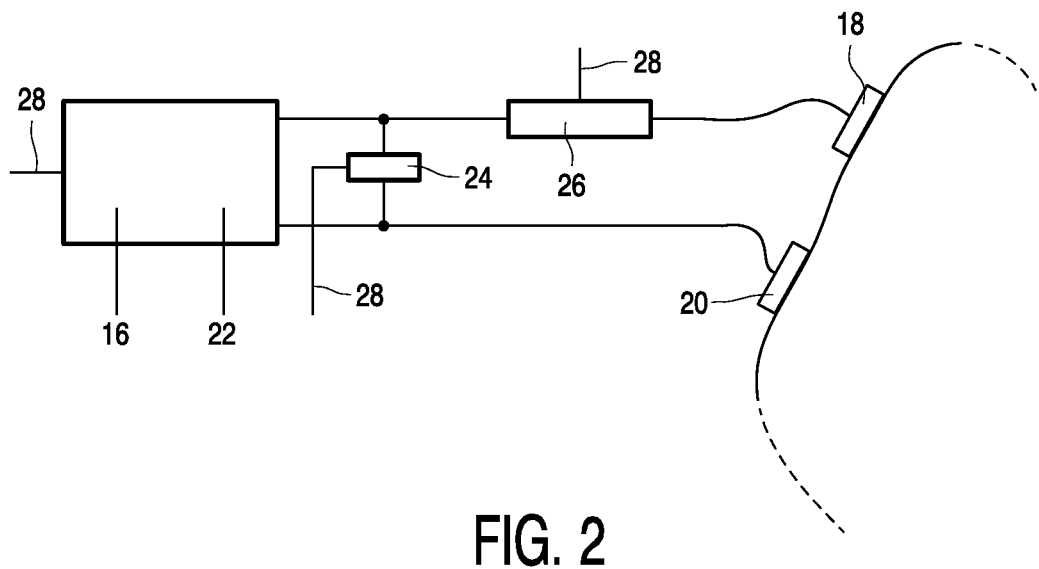

FIG. 2 shows a transmit unit 16 of the transmit and receive unit 6 in the form of a voltage generator 22, as may be used for example for local conductivity measurement. For greater clarity, only two terminal contacts 18 and 20 are shown, of which one is the signal terminal contact 18 and the other the ground terminal contact 20, which are connected via leads to a voltage generator 22. The voltage present between the contacts 18 and 20 is detected by means of the voltage measuring apparatus 24, while a suitable current measuring unit 26 may be connected therebetween for current measurement. To detect conductivity, further terminal contacts are provided on the object under examination A in the vicinity of contacts 18 and 20, these being connected via leads to a voltage measuring apparatus and forming a receive unit (not illustrated). These additional terminal contacts allow detection of the locally varying potential differences generated by the transmit unit 16. It goes without saying that not only the transmit unit 16, the receive unit, the voltage measuring apparatus 24 and the current measuring unit 26 but also the voltage measuring apparatus of the receive unit, comprising the terminal contacts for detecting the transmit signals, may be connected to a microprocessor or computer for the purpose of control or processing of the data for suitable image display (indicated by leads 28).

The features of the invention disclosed in the above description, the drawings and the claims may be fundamental to implementation of the invention in its various embodiments either individually or in any desired combination.

LIST OF REFERENCE NUMERALS

1 Device according to the invention
2 First arrangement
4 Terminal contacts
6 Transmit and receive unit
8 Second arrangement
10 Sub-zone with high magnetic field strength
12 Sub-zone with low magnetic field strength
14 Maxwell coil arrangement
16 Transmit unit
18 Signal terminal contact
20 Ground terminal contact
22 Voltage generator
24 Voltage measuring apparatus
26 Current measuring unit
28 Supply leads to a computer
A Object under examination

The invention claimed is:

1. A method of determining a three-dimensional conductivity distribution in an examination area of an object under examination, comprising:
 introducing magnetic particles into at least part of the examination area of the object under examination;
 generating an electrical field at least in part of the examination area;
 generating a magnetic field in the examination area, having a spatial magnetic field strength profile with a first sub-zone with a first magnetic field strength and a second sub-zone with a second magnetic field strength which is greater than the first magnetic field strength;
 varying a spatial position of the two sub-zones in the examination area such that a magnetization of the particles changes within the two sub-zones;
 detecting signals which depend on the magnetization in the examination area influenced by the varying of the spatial position of the two sub-zones in the examination area;
 evaluating the signals to obtain information about a spatial distribution of the magnetic particles in the examination area; and
 determining a conductivity in the examination area as a function of the spatial distribution of the magnetic particles in the examination area.

2. The method according to claim 1, wherein at least some of the magnetic particles exhibit anisotropic properties.

3. The method according to claim 2, wherein an effective anisotropy of the magnetic particles exhibits a value which is sufficient for a magnetic reversal of the particle to take place substantially by Brownian rotation.

4. The method according to claim 1, wherein the magnetic particles include a monodomain particle, which is magnetically reversible substantially via a Brownian rotation.

5. The method according to claim 1, wherein the magnetic particles include at least one of a hard- or soft-magnetic multidomain particle.

6. The method according to claim 1, wherein the magnetic particles include hard-magnetic materials.

7. The method according to claim 6, wherein the hard-magnetic materials include at least one of Al—Ni, Al—Ni—Co and Fe—Co—V alloys and barium ferrite (BaO 6xFe$_2$O$_3$).

8. The method according to claim 1, wherein the magnetic particles are in a form of at least one of: lamellae and needles.

9. The method of claim 1, wherein generating an electrical field at least in part of the examination area comprises:
 providing an electrical transmit unit, comprising at least one voltage generator, at least a first signal terminal contact, and a ground terminal; and
 connecting the first signal terminal contact and the ground terminal to the object under examination; and
 providing the electrical field by applying a voltage between the first signal terminal contact and the ground terminal.

10. The method of claim 9, wherein determining a conductivity in the examination area as a function of a magnetization status of the magnetic particles, comprises:
 connecting a third signal terminal contact and a fourth signal terminal contact to the object under examination; and
 detecting via a first voltage measurement apparatus a voltage between the third signal terminal contact and the fourth signal contact.

11. The method of claim 1, wherein determining a conductivity in the examination area as a function of a magnetization status of the magnetic particles, comprises:
 connecting a plurality of pairs of signal terminal contacts; and
 measuring a plurality of voltages between the pairs of signal terminal contacts.

12. The method of claim 1, wherein generating an electrical field at least in part of the examination area includes generating an alternating electrical field.

13. The method of claim 1, wherein generating a magnetic field having a spatial magnetic field strength profile with a first sub-zone with a first magnetic field strength and a second sub-zone with a second magnetic field strength in the examination area includes generating a magnetic gradient field which reverses direction in the first sub-zone of the examination area and exhibits a zero crossing.

14. The method of claim 13, wherein varying the spatial position of the two sub-zones in the examination area such that a magnetization of the particles changes locally comprises generating a time-variable magnetic field superimposed on the magnetic gradient field for displacing the two sub-zones in the examination area.

15. The method of claim 13, wherein varying the spatial position of the two sub-zones in the examination area such that a magnetization of the particles changes locally comprises superimposing an oscillating or rotating magnetic field at least in the first sub-zone.

16. The method of claim 13, wherein varying the spatial position of the two sub-zones in the examination area such that a magnetization of the particles changes locally comprises generating a first and at least one second magnetic field superimposed on the magnetic gradient field, wherein the first magnetic field is varied over time at a first rate with a first amplitude and the second magnetic field is varied over time at a second rate with a second amplitude, wherein the second rate is greater than the first rate and the first amplitude is greater than the second amplitude.

17. The method of claim 16, wherein the first and second magnetic fields in the examination area extend substantially perpendicularly to one another.

18. The method of claim 1, wherein the electrical field comprises an alternating electrical field having a frequency in a range from approximately 100 Hz to 500 kHz, and an oscillation or rotational frequency of the magnetic particles has a frequency in a range from approximately 100 Hz to 1 MHz.

19. The method of claim 18, further comprising converting the frequency of the alternating magnetic field by interaction with the oscillating or rotating magnetic particles into a lower-frequency field with a frequency in the range of from approximately 1 Hz to approximately 500 Hz.

20. The method of claim 1, wherein generating a magnetic field comprises generating a time-varying magnetic field having a first frequency, and wherein detecting signals which depend on the magnetization in the examination area includes detecting a signal at one or more harmonic frequencies of the first frequency which are greater than the first frequency.

* * * * *